United States Patent
Kuo et al.

(10) Patent No.: US 7,176,230 B2
(45) Date of Patent: Feb. 13, 2007

(54) SYNTHESIS OF INDOLE ANALOGS OF 1-BENZYL-3-(5'-HYDROXYMETHYL-2'-FURYL) INDAZOLE (YC-1) AS ANTI-PLATELET AGENTS

(75) Inventors: Sheng-Chu Kuo, Taichung (TW); Fang-Yu Lee, Taichung (TW); Tsang-Miao Huang, Taichung (TW); Che-Ming Teng, Taipei (TW); On Lee, Hsinchu (TW); Chin-Yi Wu, Hsinchu (TW); Chrong-Shiong Hwang, Hsinchu (TW); Chi-Ying Hung, Hsinchu (TW)

(73) Assignees: Industrial Technology Research Institute, Hsinchu (TW); Yung Shin Pharm. Ind. Co., Ltd., Taichung (TW)

( * ) Notice: Subject to any disclaimer, the term of this patent is extended or adjusted under 35 U.S.C. 154(b) by 0 days.

(21) Appl. No.: 11/274,436

(22) Filed: Nov. 15, 2005

(65) Prior Publication Data

US 2006/0106041 A1    May 18, 2006

Related U.S. Application Data

(60) Provisional application No. 60/628,328, filed on Nov. 16, 2004.

(51) Int. Cl.
*A61K 31/405* (2006.01)
*C07D 209/04* (2006.01)

(52) U.S. Cl. .................. 514/415; 548/469; 548/490
(58) Field of Classification Search .......... 548/452, 548/466, 469, 490; 514/415
See application file for complete search history.

(56) References Cited

OTHER PUBLICATIONS

Meltz, C, Volkmann, R. Boron Trifluoride activated 3-thiazolines. A versatile synthesis of thiophenes. Tetrahedron Letters, 1983, 24, 4507-4510.*
Coutoure, A, Deniau, E, Gimbert, Y, Grandclaudon, P. An expeditious synthesis of 3-alkyl, aryl-, and heteroaryl-indoles by way of an intramolecular Horner-Wittig reaction. J. Chem. Soc. Perkin Trans. I, 1993, 20, 2463-2466.*
Abarca, B, Ballesteros, R. Indoles and annulated indoles I. The preparation of some 2-substituted-3-(2'-thienyl)indoles. Anales de Quimica, 1983, 79, 23-26.*
Abarca, et al., "Indoles and annulated indoles I. The preparation of some 2-substituted-3-(2'-thienyl)indoles," 1983, vol. 79, p. 23-26.*
Chauder B, Larkin A, Snieckus V. Rapid route to 3,4-substituted indoles via a directed ortho metalation-retro-Mannich sequence. Org Lett. Mar. 7, 2002;4(5):815-7.
Chun YS, Yeo EJ, Park JW. Versatile pharmacological actions of YC-1: anti-platelet to anticancer. Cancer Lett. Apr. 15, 2004;207(1):1-7.
Ko FN, Wu CC, Kuo SC, Lee FY, Teng CM. YC-1, a novel activator of platelet guanylate cyclase. Blood. Dec. 15, 1994;84(12):4226-33.
Lee FY, Lien JC, Huang LJ, Huang TM, Tsai SC, Teng CM, Wu CC, Cheng FC, Kuo SC. Synthesis of 1-benzyl-3-(5'-hydroxymethyl-2'-furyl)indazole analogues as novel antiplatelet agents. J Med Chem. Oct. 25, 2001;44(22):3746-9.
Wu CC, Ko FN, Kuo SC, Lee FY, Teng CM. YC-1 inhibited human platelet aggregation through NO-independent activation of solube guanylate cyclase. Br J Pharmacol. Oct. 1995;116(3):1973-8.

* cited by examiner

*Primary Examiner*—Joseph K. McKane
*Assistant Examiner*—Susannah L. Chung
(74) *Attorney, Agent, or Firm*—Jackson Walker L.L.P.

(57) ABSTRACT

The present invention synthesizes a series of novel indole analogs of 1-benzyl-3-(5'-hydroxymethyl-2'-furyl)indazole (YC-1), and their anti-platelet activity.

14 Claims, 2 Drawing Sheets

Scheme 1

Scheme 2

SYNTHESIS OF INDOLE ANALOGS OF 1-BENZYL-3-(5'-HYDROXYMETHYL-2'-FURYL) INDAZOLE (YC-1) AS ANTI-PLATELET AGENTS

CROSS-REFERENCE TO RELATED APPLICATION

This application claims the benefit of U.S. Provisional Application No. 60/628,328, filed 16 Nov. 2004.

FIELD OF THE INVENTION

The present invention is related to a series of indole analogs of 1-benzyl-3-(5'-hydroxymethyl-2'-furyl)indazole (YC-1), and their anti-platelet activity.

BACKGROUND OF THE INVENTION

In a previous paper[1-3], a series of 1-benzyl-3-(5'-hydroxymethyl-2'-furyl)indazole (YC-1) derivatives were found to exhibit significant inhibitory effect against thrombin-, AA-, collagen-, and PAF-induced platelet aggregation. The broad-spectrum anti-platelet activity of YC-1 derivatives indicated that they interfered with platelet aggregation through a common pathway. Mechanism investigation revealed that such anti-platelet activity was associated with NO-independent activation of soluble guanyl cyclase (sGC)[1,2]. YC-1 was long recognized as a new anti-platelet agent with unique mechanism of action. Since the debut of our YC-1 paper, more than 150 publications related with YC-1 have been seen in the literature. Documented in these papers were the versatile pharmacological activities of YC-1 that include its anti-platelet and vasodilatorly activity via cGMP-dependent mechanisms. On the contrary, YC-1 was also reported to exert its anticancer and anti-angiogenic effects through a cGMP-independent pathway[4]. Thus, YC-1 has been recognized as an innovative drug candidate with great potential.

SUMMARY OF THE INVENTION

The present invention was undertaken to synthesize novel anti-platelet agents, the indazole ring in YC-1 was replaced by indole to form a core structure that was systematically modified to yield a variety of derivatives that were evaluated for their anti-platelet activity A first aspect of the present invention is a compound of formula (I):

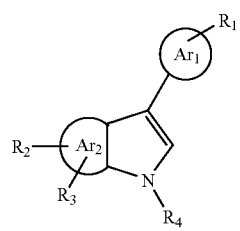

(I)

wherein $Ar_1$ is furyl, thiophene, pyrrole, phenyl, pyridinyl or pyrimidinyl, and preferably
$Ar_1$ is furyl or thiophene, and more preferably $Ar_1$ is furyl;
$Ar_2$ is benzene, pyridine or pyrimidine, and preferably $Ar_2$ is benzene;
$R_1$ is H, C1–C6 alkyl, hydroxy C1–C6 alkyl, carboxyl, alkyloxycarbonyl,

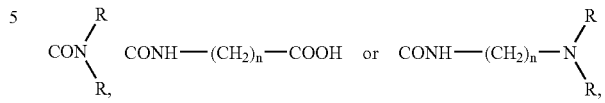

and preferably $R_1$ is hydroxy C1–C6 alkyl, and more preferably hydroxymethyl;
$R_2$ and $R_3$ independently are H, Cl, F, Br, OH, O—R,

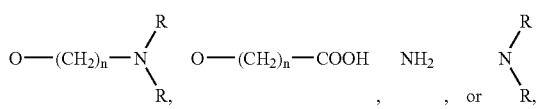

and preferably $R_2$ and $R_3$ are H;
$R_4$ is H, C1–C6 alkyl,

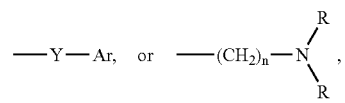

wherein Ar is C6–C14 aryl, Y is $—(CH_2)_n—$,

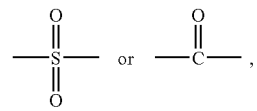

preferably $R_4$ is —Y-phenyl, and more preferably Y is

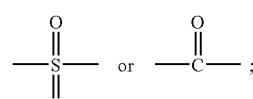

wherein R is C1–C6 alkyl, and n=1–6.

A second aspect of the present invention is a composition comprising an effective anti-platelet aggregation amount of a compound of the formula (I) above, or a pharmaceutically acceptable salt thereof, in a pharmaceutically acceptable carrier.

A further aspect of the present invention is a method for inhibiting platelet aggregation, the method comprising administering to a subject in need of treatment a compound of the formula (I) above, or a pharmaceutically acceptable salt thereof, in an amount effective to inhibit platelet aggregation.

A still further aspect of the present invention is the use of a compound of the formula (I) above, or a pharmaceutically acceptable salt thereof, for the preparation of a medicament for carrying out the method described above.

Preferably, the compound of the formula (I) above has the following formula:

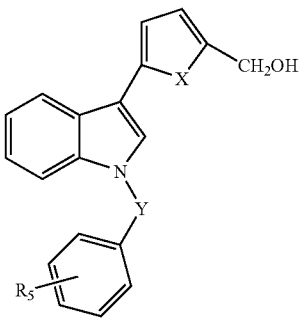

wherein X is O or S, and preferably X is O; Y is —(CH$_2$)$_n$—,

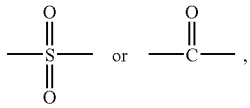

wherein n=1–6, and preferably Y is

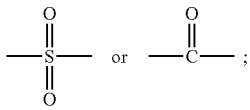

and R$_5$ is H, halogen, C1–C6 alkyl, or C1–C6 alkoxy, and preferably R$_5$ is H or C1–C6 alkoxy, such as methoxy.

Preferably, the compound of formula (I) is
'N-benzenesulfonyl-3-(5'-hydroxymethyl-2'-furyl)indole (16),
N-benzenesulfonyl-3-(5-hydroxymethyl-2'-thienyl)indole (17),
N-Benzoyl-3-(5'-hydroxymethyl-2'-furyl)indole (32),
N-(3'-Methoxybenzoyl)-3-(5'-hydroxymethyl-2'-furyl)indole (33), and
N-(4'-Methoxybenzoyl)-3-(5'-hydroxymethyl-2'-furyl)indole (34).

DETAILED DESCRIPTION OF THE INVENTION

In continuation of our research program aimed at the development of novel anti-platelet agents, the indazole ring in YC-1 was replaced by indole to form a core structure that was systematically modified to yield a variety of derivatives that were evaluated for their anti-platelet activity.

The term "alkyl" as used herein, inidividually or as a portion of another substituent term such as "alkoxy", refers to C1 to C6 alkyl, which may be linear or branched, and saturated or unsaturated. Preferably, the alkyl is saturated, and preferably the alkyl is linear.

The term "halogen" or "halo" as used herein refers to fluorine, chlorine, bromine, iodine, etc., or fluoro, chloro, bromo, iodo, etc., respectively.

Suitable methods for synthesizing the compounds of the present invention will be described in the following, and variations thereof will be apparent to those skilled in the art in given the Examples set forth below.

Figure 1:
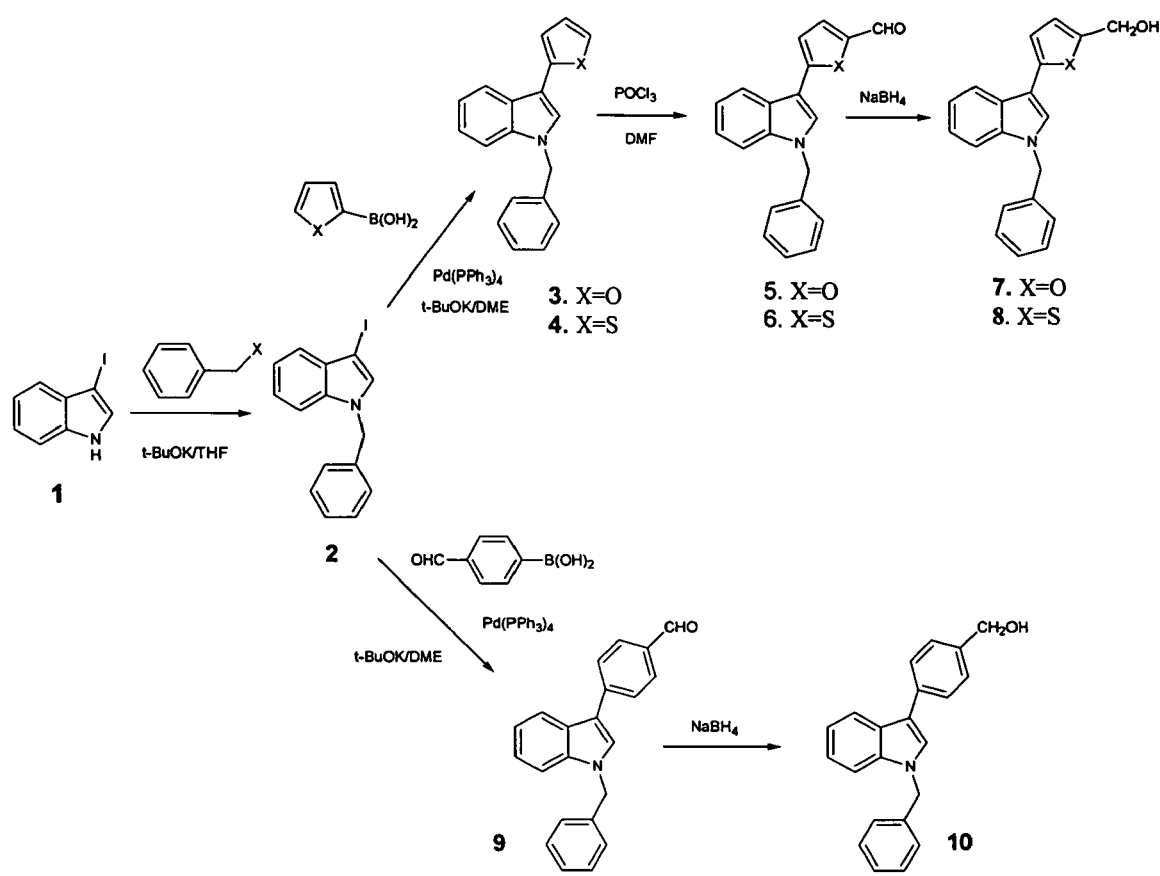
FIG. 1 shows a chemical reaction scheme for synthesizing N-Substituted benzyl-3arylindoles derivatives (compounds 7–8, and 10) of the present invention.

N-Substituted benzyl-3arylindoles derivatives (7–8, 10) were synthesized according to Scheme 1, shown in FIG. 1. First, the starting material 3-iodoindole (1)[5] was alkylated with various substituted benzyl halides to afford the corresponding N-substituted benzyl-3-iodoindoles (2) which were then subjected to Suzuki-type coupling reaction with a variety of arylboronic acids to yield the key intermediates 3-furyl-(3), 3-thienyl-(4), and 3-(4-formylphenyl)-derivatives (9). Then, the conversion of compounds 3 and 4, to target compounds N-benzyl-3-(5'-hydroxymethyl-2'-furyl)indole (7) and N-benzyl-3-(5'-hydroxymethyl-2'-thienyl)indole (8), was accomplished via Vielsmeir formylation, followed by reduction. Meanwhile, the direct reduction of compound 9 provided another series of target compounds N-benzyl-3-(4-hydroxymethylphenyl)indole (10).

Figure 2:
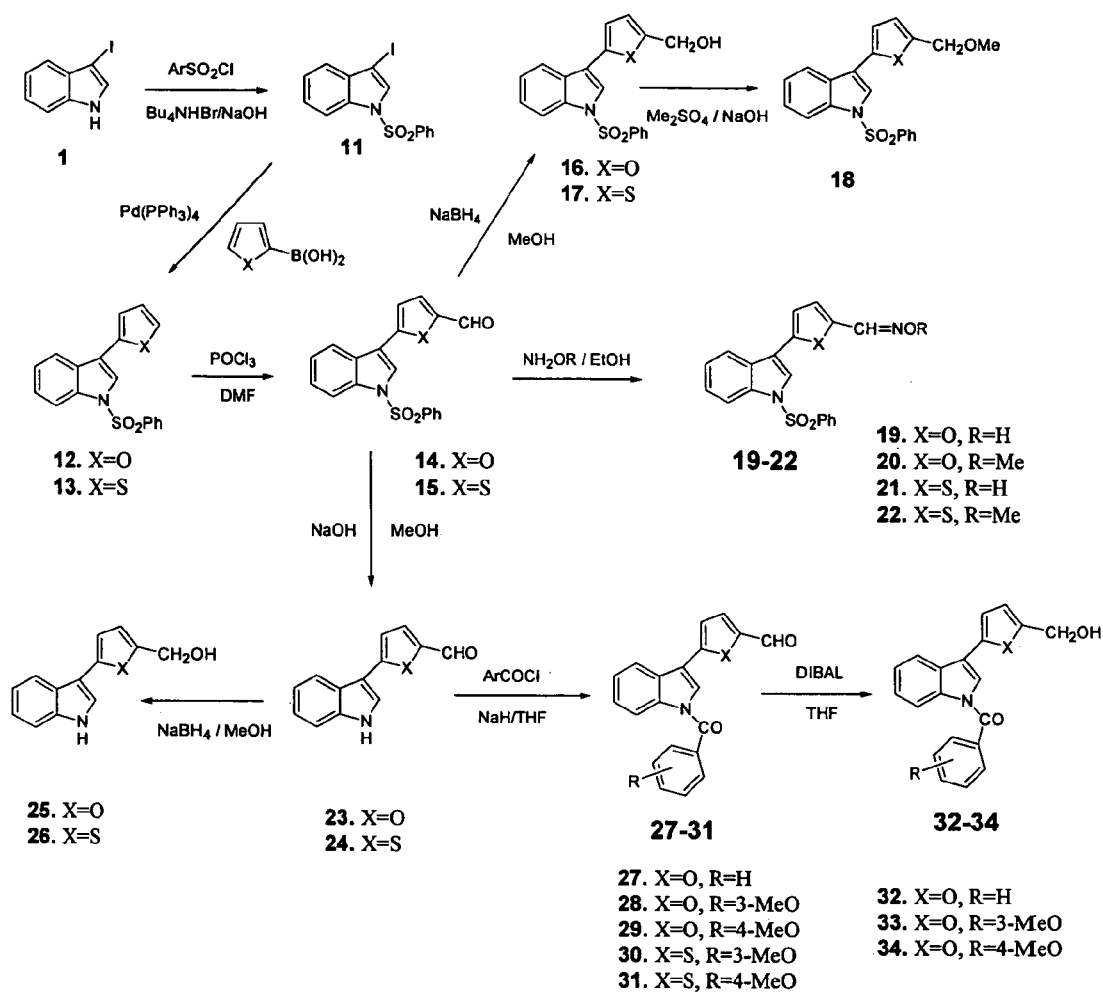
FIG. 2 shows a chemical reaction scheme for synthesizing N-Substituted benzyl-3arylindoles derivatives (compounds 18–22, and 32–34) of the present invention

N-Sulfonyl indazoles (16, 17) and N-benzoyl indazoles (32–34) derivatives were prepared according to Scheme 2, shown in FIG. 2. As shown, compound 1 was first sulfonated with a variety of sulfonating agents to afford the corresponding N-sulfonyl-3-iodoindazoles (11)[5] that were subsequently converted to 3-furyl (12), or 3-thienyl (13) derivatives, via Suzuki-type coupling with furan-2-boronic acid or thiophene-2-boronic acid, respectively. Then, the formylation of compounds 12 and 13, followed by reduction, gave the corresponding target compounds N-benzenesulfonyl-3-(5'-hydroxymethyl-2'-furyl)indole (16) and N-benzenesulfonyl-3-(5-hydroxymethyl-2'-thienyl)indole (17). Afterwards, compounds 16 and 17 were subjected to O-methylation to produce the corresponding O-methoxymethyl derivatives (18). In a separate route, the intermediates 14 and 15 were treated with hydroxylamines to afford the corresponding Schiff's base products (19, 22). At the same time, the intermediates 14 and 15 were subjected to desulfonation with NaOH to produce another two key intermediates (23, 24). Subsequent acylation of 23 and 24, followed by reduction, gave another set of targeted N-benzoyl derivatives (32–34). Alternatively, intermediates 23 and 24 were reduced into compounds 3-(5'-hydroxy-methyl-2'-furyl)indole (25) and 3-(5'-hydroxymethyl-2'-thienyl)indole (26), respectively.

The following Examples are provided to further illustrate the present invention, and should not be construed as limiting thereof. All starting materials were commercially available. Solvents and reagents were used without further purification. Reactions were monitored by either TLC on silica gel plastic sheets (Kieselgel 60 F$_{254}$, Merck) or HPLC. Purification was performed by flash chromatography using silica gel (particle size 63–200 µm, Merck). NMR spectra were recorded on a Varian 500-MHz spectrometer. Chemical shifts are reported as ppm (δ) relative to TMS as internal standard. Mass spectra were recorded on a JEOL JMS-SX102A spectrometer (HREI). IR spectra were recorded on a Horiba FT-730 FT-IR spectrometer. Melting points were determined on a Buchi B-540 apparatus and are uncorrected.

EXAMPLES

General Procedure of N-Alkylation in Base

N-benzyl-3-Iodoindole (2)

To a solution of 3-iodoindole (1, 2.9 g, 11.93 mmol) in THF (50 mL) is added t-BuOK (1.6 g, 14.26 mmol) at 0° C. After 1 h, PhCH$_2$Br (3.0 g, 17.54 mmol) is added dropwise over 20 min at 0° C. The reaction is then warmed to room temperature and stirred for additional 4 h, then concentrated under reduced pressure. The residue is partitioned between EtOAc (60 mL) and H$_2$O (30 mL). The organic layer is dried (MgSO$_4$). The solvent is then removed and purification by flash column chromatography from EtOAc-n-hexane to give 1.98 g (52%) of 2: $^1$H NMR (CDCl$_3$): δ7.94–7.98 (m, 1H), 7.41–7.45 (m, 2H), 7.13–7.35 (m, 5H), 6.47–6.54 (m, 2H), 5.33 (s, 2H).

N-Benzenesulfonyl-3-iodoindole (11)[5]

To a solution of NaOH (8.7 g, 0.22 mol) dissolved in water (35 mL) and Bu$_4$NHBr (0.8 g, 2.48 mmol) is added 3-iodoindole (4.1 g, 16.8 mmol) at 0° C., then benzenesulfonyl chloride (3.9 g, 22.1 mm) in THF (20 mL) is added dropwise. The mixture is allowed to react for 3 h at room temperature. The mixture is extracted with ethyl acetate. The extract is dried with magnesium sulfate, and then concentrated. Purification by flash column chromatography from EtOAc-n-hexane affords 4.9 g (77%) of 11: $^1$H NMR (CDCl$_3$): δ8.22 (d, 1H, J=8.03 Hz), 7.81 (d, 2H, J=7.91 Hz), 7.18–7.54 (m, 7H).

General Procedure of Suzuki Coupling (Pd(PPh$_3$)$_4$/Base)

N-Benzyl-3-furylindole (3)

A solution of compound (2, 0.5 g, 1.5 mmol) in DME (30 mL) and THF (10 mL) is heated at reflux under argon with 2-furanboronic acid (0.33 g, 2.95 mmol), Pd(PPh$_3$)$_4$ (85 mg, 0.073 mmol) and t-BuOK (0.66 g, 5.88 mmol) in degassed for 20 h. After cooling to room temperature, the mixture is filtered on a celite column and vacuum evaporation to give the crude product which is purified by chromatography (silica gel, EtOAc/n-hexane) to obtain 0.062 g (34%) of 3: $^1$H NMR (CDCl$_3$): δ7.94–7.99 (m, 1H), 7.75 (s, 1H), 7.54 (d, 1H, J=4.32 Hz), 7.44–7.48 (m, 1H), 7.12–7.32 (m, 7H), 6.63 (d, 1H, J=8.49 Hz), 6.52–6.54 (m, 1H), 5.49 (s, 2H).

N-Benzyl-3-thiophenylindole (4)

N-Benzyl-3-iodoindole (2), 2-thiopheneboronic acid, Pd(PPh$_3$)$_4$ and K$_2$CO$_3$ in toluene are allowed to react in the same manner as described in the preparation of compound 3 to give 0.054 g (28%) of 4: $^1$H NMR (CDCl$_3$): δ7.90–7.94 (m, 1H), 7.02–7.27 (m, 12H), 5.24 (s, 2H).

N-Benzenesulfonyl-3-furylindole (12)

N-Benzenesulfonyl-3-iodoindole (11), 2-furanboronic acid, Pd(PPh$_3$)$_4$ and K$_2$CO$_3$ in toluene are allowed to react in the same manner as described in the preparation of compound 3 to give 0.29 g (69%) of 12: $^1$H NMR (CDCl$_3$): δ8.04 (d, 1H, J=7.53 Hz), 7.87–7.93 (m, 3H), 7.26–7.57 (m, 7H), 6.66 (d, 1H, J=3.23 Hz), 6.50–6.52 (m, 1H).

N-Benzenesulfonyl-3-thienylindole (13)

N-Benzenesulfonyl-3-iodoindole (11), 2-thiopheneboronic acid, Pd(PPh$_3$)$_4$ and K$_2$CO$_3$ in toluene are allowed to react in the same manner as described in the preparation of compound 3 to give 0.33 g (75%) of 13: $^1$H NMR (CDCl$_3$): δ7.97 (d, 1H, J=8.16 Hz), 7.79–7.16 (m, 3H), 7.70 (s, 1H), 7.18–7.46 (m, 7H), 7.03–7.08 (m, 1H).

N-Benzyl-3-(P'-formylphenyl)indole (9)

N-Benzyl-3-iodoindole (2), 4-formylphenylboronic acid, Pd(OAc)$_2$(dppf) and t-BuOK in DME are allowed to react in the same manner as described in the preparation of compound 3 to give 9 in 75% yield. mp 121–122° C.; IR (cm$^{-1}$): 2924, 1700; $^1$H NMR (CDCl$_3$): δ10.00 (s, 1H), 7.80–8.03 (m, 4H), 7.17–7.45 (m, 10H), 5.39 (s, 2H); HRMS: m/z 311.1310 (calculated for C$_{22}$H$_{17}$NO, 311.1310).

General Procedure of Formylation (POCl$_3$/DMF)

N-Benzyl-3-(5'-formyl-2'-furyl)indole (5)

To a flask is placed N,N-dimethylformamide (1.1 mL, 13 mmol) while the flask is cooled to 0° C. Phosphorus oxychloride (1.8 g, 12 mmol) is added dropwise with stirring. After 1 h, compound 3 is added to the flask. The solution is heated at 50° C. for 1 h. The reaction mixture is then cooled to room temperature and poured over crushed ice in beaker, and neutralized to pH 7–8 with 6N sodium hydroxide. The mixture is extracted with ethyl acetate. The extract is dried with magnesium sulfate, and then concentrated. The residue is purified by chromatography on silica gel (EtOAc/n-hexane) to obtain 5 as a solid; yield: 0.22 g (66%): mp 144° C.; IR (cm$^{-1}$): 1736; $^1$H NMR (CDCl$_3$): δ 9.57 (s, 1H), 8.06–8.11 (m, 2H), 7.22–7.31 (m, 8H), 6.91–6.93 (d, 2H), 5.55 (s, 2H). HRMS: m/z 301.1100 (calculated for C$_{20}$H$_{15}$NO$_2$, 301.1103).

N-Benzyl-3-(5'-formyl-2'-thienyl)indole (6)

N-Benzyl-3-thienylindole 4, N,N-dimethylformamide and phosphorus oxychloride are allowed to react in the same manner as described above in the preparation of compound 5 to afford compound 6 in 67% yield. mp=132° C.; IR (cm$^{-1}$): 1656; $^1$H NMR (CDCl$_3$): δ 9.87 (s, 1H); 7.54 (s, 1H); 8.03–8.07 (m, 1H), 7.26–7.37 (m, 7H), 7.73–7.75 (d, 1H), 7.15–7.20 (m, 2H), 5.36 (s, 2H). HRMS: m/z 317.0870 (calculated for C$_{20}$H$_{15}$NOS, 317.0874).

N-Benzenesulfonyl-3-(5'-formyl-2-furyl)indole (14)

N-Benzenesulfonyl-3-furylindole 12, N,N-dimethylformamide and phosphorus oxychloride are allowed to react in the same manner as described above in the preparation of compound 5 to afford compound 14 in 88% yield. mp 189° C.; IR (cm$^{-1}$) 2984, 1740, 1240; $^1$H NMR (CDCl$_3$): δ 9.59 (s, 1H); 7.86–8.06 (m, 4H), 7.26–7.50 (m, 6H), 7.18 (s, 1H), 6.76–6.78 (d, 1H). HRMS: m/z 351.0567 (calculated for C$_{19}$H$_{13}$NO$_4$S, 351.0565).

N-Benzenesulfonyl-3-(5'-formyl-2-furyl)indole (15)

N-Benzenesulfonyl-3-thienylindole 13, N,N-dimethylformamide and phosphorus oxychloride are allowed to react in the same manner as described above in the preparation of compound 5 to afford compound 15 in 48% yield. mp 140°

C.; IR (cm$^{-1}$): 1732, 1265; $^1$H NMR (CDCl$_3$): δ 9.91 (s, 1H), 7.88–8.08 (m, 4H), 7.77–7.79 (d, 1H), 7.26–7.61 (m, 6H). HRMS: m/z 367.0334 (calculated for C$_{19}$H$_{13}$NO$_3$S$_2$, 367.0337).

General Procedure for Aldehyde Reduction (NABH$_4$)

N-Benzyl-3-(5'-hydroxymethyl-2'-furyl)indole (7)

To a solution of compound 7 (0.034 g, 0.16 mmol) in MeOH (4 mL) is cooled by ice water and NaBH$_4$ (0.073 g, 1.8 mmol) is added. The mixture is allowed to react at room temperature for 2 h and concentrated. The mixture is extracted with ethyl acetate (40 mL). The extract is washed with water, dried with MgSO$_4$, and then concentrated. The residue is purified by column chromatography on silica gel (EtOAc/n-hexane) to obtain 7 as a white solid; yield: 0.31 g (83%): mp 134–135° C.; IR (cm$^{-1}$): 3630, 1265; $^1$H NMR (CDCl$_3$): δ 7.96–7.99 (d, 1H), 7.71 (s, 1H), 7.44–7.47 (m, 1H), 7.16–7.27 (m, 8H), 6.56 (s, 1H), 6.38 (s, 1H), 5.47 (s, 2H), 4.60 (s, 2H). HRMS: m/z 303.1261 (calculated for C$_{20}$H$_{17}$NO$_2$, 303.1259).

N-Benzyl-3-(5'-hydroxymethyl-2'-thienyl)indole (8)

N-Benzyl-3-(5'-formyl-2'-thienyl)indole (6, 42 mg, 0.13 mmol), NaBH4 (89 mg, 2.3 mmol) are allowed to react in the same manner as described above in the preparation of compound 7 to afford compound 8 in 95% yield. mp 133–134° C.; IR (cm$^{-1}$): 2993, 1750, 1242; $^1$H NMR (CDCl$_3$): δ 7.88–7.93 (m, 1H), 7.04–7.25 (m, 10H), 6.91–6.93 (d, 1H), 5.26 (s, 2H), 4.76 (s, 2H); HRMS: m/z 319.1036 (calculated for C$_{20}$H$_{17}$NOS, 319.1031).

N-Benzyl-3-(4-hydroxymethylphenyl)indole (10)

N-Benzyl-3-(4-formylphenyl)indole (9) and NaBH$_4$ are allowed to react in the same manner as described above in the preparation of compound 7 to afford compound 10 in 51% yield. mp 122° C.; IR (cm$^{-1}$): 3462, 1742; $^1$H NMR (CDCl$_3$): δ 7.94–7.97 (m, 1H), 7.64–7.68 (d, 3H), 7.41–7.45 (d, 10H), 5.34 (s, 2H), 4.72 (s, 2H). HRMS: m/z 313.1466 (calculated for C$_{22}$H$_{19}$NO, 313.1467).

N-Benzenesulfonyl-3-(5'-hydroxymethyl-2'-furyl)indole (16)

N-Benzenesulfonyl-3-(5'-formyl-2'-furyl)indole (14) and NaBH$_4$ in MeOH are allowed to react in the same manner as described above in the preparation of compound 7 to afford compound 16 in 77% yield. mp 50–50.5° C.; IR (cm$^{-1}$): 3630, 2359; $^1$H NMR (CDCl$_3$): δ 7.94–7.98 (d, 1H); 7.74–7.86 (m, 4H), 7.18–7.49 (m, 5H), 6.53–6.53 (d, 1H, J=3.4 Hz), 6.33–6.34 (d, 1H, J=3.4 Hz), 4.71 (s, 2H). HRMS: m/z 353.0720 (calculated for C$_{19}$H$_{15}$NO$_4$S, 353.0722).

N-Benzenesulfonyl-3-(5'-hydroxymethyl-2'-thienyl)indole (17)

N-Benzenesulfonyl-3-(5'-formyl-2'-thienyl)indole (15) and NaBH$_4$ in MeOH are allowed to react in the same manner as described above in the preparation of compound 7 to afford compound 17 in 79% yield. mp 60–60.5° C.; IR (cm$^{-1}$): 3480, 1741; $^1$H NMR (CDCl$_3$): δ 7.65–7.97 (m, 5H), 6.91–7.36 (m, 7H), 4.76 (s, 2H). HRMS: m/z 369.0494 (calculated for C$_{19}$H$_{15}$NO$_3$S$_2$, 369.0494).

3-(5'-Hydroxymethyl-2'-furyl)indole (25)

3-(5'-Formyl-2'-furyl)indole 23 and NaBH$_4$ in MeOH are allowed to react in the same manner as described above in the preparation of compound 7 to afford compound 25 in 85% yield. mp 210–215° C.; IR (cm$^{-1}$): 3462; $^1$H NMR (CDCl$_3$): δ 8.37 (s, 1H), 7.81–7.85 (m, 1H), 7.13–7.42 (m, 4H), 6.39–6.42 (d, 1H), 6.30–6.39 (d, 1H), 4.59 (s, 2H). HRMS: m/z 213.0778 (calculated for C$_{13}$H$_{11}$NO$_2$, 213.0790).

3-(5'-Hydroxymethyl-2'-thienyl)indole (26)

3-(5'-Formyl-2'-thienyl)indole 24 and NaBH$_4$ in MeOH are allowed to react in the same manner as described above in the preparation of compound 7 to afford compound 26 in 83% yield. mp 108–109.5° C.; IR (cm$^{-1}$): 3460; $^1$H NMR (CDCl$_3$): δ 8.27 (s, 1H), 7.87–7.90 (d, 1H), 6.91–7.32 (m, 6H), 4.75 (s, 2H). HRMS: m/z 229.0564 (calculated for C$_{13}$H$_{11}$NOS, 229.0561).

N-Benzoyl-3-(5'-hydroxymethyl-2'-furyl)indole (32)

N-Benzoyl-3-(5'-formyl-2'-furyl)indole 27 and DIBAL in THF are allowed to react in the same manner as described above in the preparation of compound 7 to afford compound 32 in 70% yield; IR (cm$^{-1}$): 3566; $^1$H NMR (CDCl$_3$): δ 8.3–8.7 (m, 1H), 7.7–8.1 (m, 1H), 7.3–7.6 (m, 8H), 6.4 (d, 1H, J=3.1 Hz), 6.3 (d, 1H, J=3.1 Hz), 4.6 (d, 2H, J=3.7 Hz). HRMS: m/z 317.1062 (calculated for C$_{20}$H$_{15}$NO$_3$, 317.1052).

N-(3'-Methoxybenzoyl)-3-(5'-hydroxymethyl-2'-furyl)indole (33)

N-(3'-Methoxybenzoyl)-3-(5'-formyl-2'-furyl)indole 28 and DIBAL in THF are allowed to react in the same manner as described above in the preparation of compound 7 to afford compound 33 in 91% yield. IR (cm$^{-1}$): 3857; $^1$H NMR (CDCl$_3$): δ 8.35–8.47 (m, 2H), 7.82–7.92 (m, 2H), 7.58 (s, 1H); 7.11–7.43 (m, 4H), 6.60 (d, 1H, J=3.5 Hz), 6.40 (d, 1H, J=3.5 Hz), 4.63 (s, 2H), 3.82 (s, 3H). HRMS: m/z 347.1156 (calculated for C$_{21}$H$_{17}$NO$_4$, 347.1158).

N-(4'-Methoxybenzoyl)-3-(5'-hydroxymethyl-2'-furyl)indole (34)

N-(4'-Methoxybenzoyl)-3-(5'-formyl-2'-furyl)indole 29 and DIBAL in MeOH are allowed to react in the same manner as described above in the preparation of compound 7 to afford compound 34 in 58% yield. IR (cm$^{-1}$) 3636, 1746; $^1$H NMR (CDCl$_3$): δ 8.2–8.4 (m, 2H), 7.8–7.9 (m,2H), 7.6–7.7 (m, 2H), 7.1–7.5 (m, 8H), 7.0 (d, 2H, J=8.7 Hz), 6.8 (d, 2H, J=8.7 Hz), 6.5 (d, 2H, J=3.5 Hz), 6.3 (d, 2H, J=3.5 Hz), 4.6 (s, 3H), 4.5 (s, 3H), 3.8 (s, 3H), 3.7 (s, 3H). HRMS: m/z 347.1130 (calculated for C$_{21}$H$_{17}$NO$_4$, 347.1158).

General Procedure for Oxime Synthesis (RONH$_2$.HCl)

N-Benzenesulfonyl-3-(5'-formyl-2'-furyl)indole O-methyloxime (20)

To a round-bottom flask is charged with 1-benzenesulfonyl-3-(5'-formyl-2'-furyl)indole 14 (0.1 g, 0.28 mmol) and MeONH$_2$.HCl (48 mg, 0.57 mmol) in ethanol (6 mL). The solution is allowed to react for 16 h at room temperature, and then concentrated. The mixture is extracted with ethyl acetate (40 mL). The extract is washed with water, dried over $MgSO_4$, and then concentrated to compound 20 as a white solid; yield: 0.11 g (95%): $^1$H NMR ($CDCl_3$): 7.3–7.2 (m, 4H), 6.5–6.9 (m, 6H), 6.2 (d, 1H, J=3.5 Hz), 6.1 (d, 1H, J=3.5 Hz), 4.8 (s, 1H), 3.1 (s, 3H). HRMS: m/z 380.0829 (calculated for $C_{20}H_{16}N_2O_4S$, 380.0831).

1-Benzenesulfonyl-3-(5'-methyloxime-2'-furyl)indole (19)

1-Benzenesulfonyl-3-(5'-formyl-2'-furyl)indole (14) and $HONH_2·HCl$ in ethanol are allowed to react in the same manner as described above in the preparation of compound 20 to afford compound 19 in 93% yield. IR ($cm^{-1}$): 3409, 1746; $^1$H NMR ($CDCl_3$): δ 9.7 (s, 1H), 7.3–7.4 (m, 4H), 6.6–7.0 (m, 6H), 6.2 (d, 1H, J=3.5 Hz), 6.1 (d, 1H, J=3.5 Hz), 4.8 (s, 1H). HRMS: m/z 366.0670 (calculated for $C_{19}H_{14}N_2O_4S$, 366.0674).

1-Benzenesulfonyl-3-(5'-formyl-2'-thienyl)indole O-methyl oxime (22)

1-Benzenesulfonyl-3-(5'-formyl-2'-thienyl)indole (15) and $MeONH_2·HCl$ in ethanol are allowed to react in the same manner as described above in the preparation of compound 20 to afford compound 22 in 95% yield. mp 114–116° C.; IR ($cm^{-1}$): 2984, 1746; $^1$H NMR ($CDCl_3$): 2-isomers; HRMS: m/z 396.0605 (calculated for $C_{20}H_{16}N_2O_3S_2$, 396.0602).

1-Benzenesulfonyl-3-(5'-formyl-2'-thienyl)indole oxime (21)

1-Benzenesulfonyl-3-(5'formyl-2'-thienyl)indole (15) and $HONH_2·HCl$ in ethanol are allowed to react in the same manner as described above in the preparation of compound 20 to afford compound 21 in 50% yield. mp 173.8–174.1° C.; IR ($cm^{-1}$) 3724, 2359, 1736: $^1$H NMR ($CDCl_3$): δ 7.24 (s, 1H), 6.70–7.01(m, 6H), 6.13–6.51(m, 7H). HRMS: m/z 382.0443 (calculated for $C_{19}H_{14}N_2O_3S_2$, 382.0446).

General Procedure for N-1 Desulfonation (2N NAOH/MEOH)

3-(5'-Formyl-2'-thienyl)indole (24)

1-Benzenesulfonyl-3-(5'-formyl-2'-thienyl)indole (15, 0.85 g, 2.32 mmol) is dissolved in a mixture of methanol (90 mL) and 2N sodium hydroxide solution (10 mL) at 70° C. for 3 h, then concentrated. The mixture is extracted with ethyl acetate (40 mL). The extracts is washed with water, dried over $MgSO_4$, and then concentrated. The solid is washed with n-hexane to obtain compound 24 as a white solid; yield: 0.47 g (89%): mp 170° C.; IR ($cm^{-1}$): 1740, 1240: $^1$H NMR ($CDCl_3$): 9.80 (s, 1H), 7.72–8.02 (m, 3H), 7.23–7.53 (m, 5H). HRMS: m/z 227.0611 (calculated for $Cl_{13}H_9NOS$, 227.0605).

3-(5'-Formyl-2'-furyl)indole (23)

1-Benzenesulfonyl-3-(5'-formyl-2'-furyl)indole (14), 2N sodium hydroxide solution in MeOH are allowed to react in the same manner as described above in the preparation of compound 24 to afford compound 23 in 95% yield. mp 187° C.; IR ($cm^{-1}$): 1669; $^1$H NMR ($CDCl_3$): δ 9.47 (s, 1H); 7.96–8.00 (m, 1H), 7.85 (s, 1H), 7.39–7.50 (m, 2H), 7.24–7.28 (m, 2H), 6.75–6.77 (d, 1H). HRMS: m/z 211.0633 (calculated for $C_{13}H_9NO_2$, 211.0633).

General Procedure for N-1 Acylation (ARCOCL/NAH)

N-Benzoyl-3-(5'-formyl-2'-thienyl)indole (30)

The solution of 3-(5'-formyl-2'-thienyl)indole (24, 0.1 g, 0.47 mmol) in anhydrous THF (12 mL) is added dropwise to a suspension of 80% NaH in THF (0.05 g, 0.22 mmol) at 0° C. over 20 minutes. The mixture is allowed to react for further 30 minutes at this temperature, and then 3-methoxybenzoylchloride (0.16 g, 0.94 mmol) is added and stirring at room temperature for another 3 h. The reaction mixture is then concentrated and the residue is extracted with ethyl acetate (40 mL). The extracts is washed with water, dried over $MgSO_4$, and then concentrated. The residue is purified by column chromatography on silica gel (EtOAc/n-hexane) to obtain 30 as a white solid; yield: 0.075 g (47%): mp 105–107° C.; IR ($cm^{-1}$): 1695; $^1$H NMR ($CDCl_3$): δ 9.5 (s, 1H), 9.83 (s, 1H), 8.33–8.35 (m, 1H), 7.88–7.92 (m, 1H), 7.60–7.70 (d, 1H), 7.52 (s, 1H), 7.09–7.44 (m, 6H), 3.81 (s, 3H). HRMS: m/z 361.0778 (calculated for $C_{21}H_{15}NO_3S$, 361.0773).

N-Benzoyl-3-(5'-formyl-2'-furyl)indole (27)

3-(5'-Formyl-2'-furyl)indole (23), benzoyl chloride, 80%NaH in THF are allowed to react in the same manner as described above in the preparation of compound 30 to afford compound 27 in 81% yield. IR ($cm^{-1}$): 1718, 1675; $^1$H NMR ($CDCl_3$): δ 9.5 (s, 1H), 8.2–8.4 (m, 1H), 6.8–7.8 (m, 10H), 6.8 (d, 1H, J=3.7 Hz). HRMS: m/z 315.0894 (calculated for $C_{20}H_{13}NO_3$, 315.0895).

N-(3'-Methoxybenzoyl)-3-(5'-formyl-2'-furyl)indole (28)

3-(5'-Formyl-2'-furyl)indole (23), 80%NaH and m-methoxy-benzoyl chloride in THF are allowed to react in the same manner as described above in the preparation of compound 30 to obtain compound 28 in 95% yield. mp 149° C.; IR ($cm^{-1}$): 1751: $^1$H NMR ($CDCl_3$): δ 9.5 (s, 1H), 8.0–8.4 (m, 1H), 7.8–8.0 (m, 1H), 7.1–7.4 (m, 8H), 6.8 (d, 1H, J=3.7 Hz), 3.8 (m, 3H). HRMS: m/z 345.1018 (calculated for $C_{21}H_{15}NO_4$, 345.1001).

N-(4-Methoxybenzoyl)-3-(5'-formyl-2'-furyl)indole (29)

3-(5'-Formyl-2'-furyl)indole (23), 80%NaH and p-methoxy-benzoyl chloride in THF are allowed to react in the same manner as described above in the preparation of compound 30 to afford compound 29 in 54% yield. IR ($cm^{-1}$) 1737; $^1$H NMR ($CDCl_3$): δ 9.6 (s, 1H); 8.2–8.4 (m, 2H), 7.6–8.1 (m, 4H), 7.2–7.5 (m, 3H), 7.0 (d, 1H, J=3.5 Hz), 6.8 (d, 1H, J=3.5 Hz), 3.8 (s, 3H). HRMS: m/z 345.1021 (calculated for $C_{21}H_{15}NO_4$, 345.1001).

N-(4-Methoxybenzoyl)-3-(5'-formyl-2'-thienyl)indole (31)

3-(5'-Formyl-2'-thienyl)indole (24), 80% NaH and p-methoxybenzoyl chloride in THF are allowed to react in the same manner as described above in the preparation of compound 30 to afford compound 31 in 95% yield. mp 163.1–163.5° C.; IR (cm$^{-1}$) 2985, 1746; $^1$H NMR (CDCl$_3$): δ 9.83 (s, 1H); 8.33–8.38(m, 1H), 7.70–7.92 (m, 1H), 7.60–7.70 (d, 1H), 7.34–7.44 (m, 4H), 7.09–7.29 (m, 3H), 3.81 (s, 3H). HRMS: m/z 361.0771 (calculated for C$_{21}$H$_{15}$NO$_3$S, 361.0773).

N-Benzenesulfonyl-3-(5'-methoxymethyl-2'-furyl) indole (18)

Dimethyl sulfate (0.14 g, 1.11 mmol) is added dropwise to the N-benzenesulfonyl-3-(5'-hydroxymethyl-2'-furyl)indole (16, 0.2 g, 0.57 mmol) in a mixture of ethylene chloride (8 mL) and 50% sodium hydroxide solution (0.7 mL), then refluxed for 16 h. The reaction mixture is cooled to room temperature and poured into ice (10 g). The mixture is extracted with ethyl acetate (40 mL) and the extract is dried over MgSO$_4$, and then concentrated. The residue is purified by column chromatography on silica gel (EtOAc/n-hexane) to obtain 18. yield: 0.186 g (88%): IR (cm$^{-1}$): 2359 ; $^1$H NMR (CDCl$_3$): δ 8.2–8.3 (m, 1H), 7.8–8.0 (m, 4H), 7.2–7.4 (m, 5H), 6.5 (d, 1H, J=3.4 Hz), 6.4 (d, 1H, J=3.4 Hz), 4.4 (s, 2H), 3.4 (s, 3H). HRMS: m/z 367.0875 (calculated for C$_{20}$H$_{17}$NO$_4$S, 367.0878).

BIOLOGICAL METHODS

Materials

Evaluation of Antiplatelet Aggregation Activity

Collagen (type 1, bovine Achilles tendon), obtained from Sigma Chemical Co., was homogenized in 25 mL HOAc and stored at −70° C. Arachidonic acid, bovine serum albumin (BSA), EDTA (disodium salt), sodium citrate, dimethyl sulfoxide (DMSO), and platelet activating factor (PAF) were purchased from Sigma Chemical Co. Thrombin (bovine) was obtained from Parke-Davis Co. and dissolved in 50% (v/v) glycerol to give a stock solution of 100 NIH units/mL.

Platelet Suspension Preparation

Blood was collected from the rabbit marginal ear vein and was mixed with EDTA to a final concentration of 6 mM. It was centrifuged at 90 g for 10 min at room temperature, and the supernatant was obtained as platelet-rich plasma. The latter was further centrifuged at 500 g for 10 min. The platelet pellets were washed with Tyrode's solution without EDTA. After centrifugation at the same conditions, the platelet pellets were finally suspended in Tyrode's solution of the following composition (mM): NaCl (136.8), KCl (2.81, NaHCO$_3$ (11.9), MgCl$_2$ (1.1), NaH$_2$PO$_4$ (0.33), CaCl$_2$ (1.0), and glucose (11.2). Platelet numbers were counted by Coulter Counter (Model ZM) and adjusted to 4.5×108 platelets/mM.

Platelet Aggregation

Aggregation was measured by the turbidmetric method with a dual-channel Lumiaggregometer (Model 1020, Payton, Canada). All glassware was siliconized. One minute before the addition of the aggregation inducer, the platelet suspension was stirred at 900 rpm. The percentage of aggregation was calculated as described previously.

Inhibitory Effect of Compounds 7, 8, 16, 17, 32–34, and 10 together with the control YC-1 and YD-1 on Platelet Aggregation Induced by Thrombin, AA, Collagen and PAF is summary in Table 1.

TABLE 1

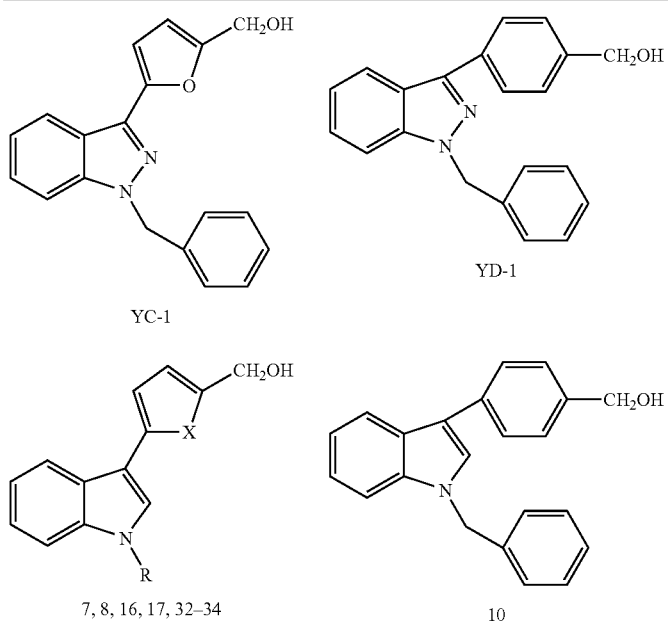

| compd | R | X | Thrombin | AA | Collagen | PAF |
|---|---|---|---|---|---|---|
| YC-1 | | | 180.0 | 57.0 | 54.6 | 90.0 |
| YD-1 | | | 192.7 | 100.9 | 122.6 | 142.9 |

TABLE 1-continued

| | | | | | | |
|---|---|---|---|---|---|---|
| 7 | 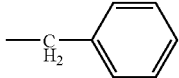 | O | >300 | >300 | >300 | >300 |
| 8 | 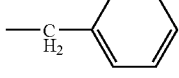 | S | >300 | >300 | >300 | >300 |
| 16 | 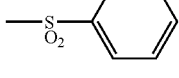 | O | 172.7 | 94.9 | 73.7 | 163.8 |
| 17 | 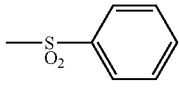 | O | >300 | 153.6 | 130.6 | 171.1 |
| 32 | 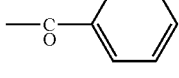 | O | >300 | 38.2 | 51.1 | >300 |
| 33 | 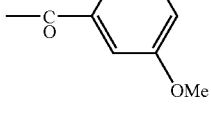 | O | 174.8 | 90.9 | 83.9 | 168.8 |
| 34 | 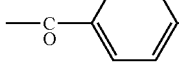 | O | >300 | 2.9 | 30.9 | 270.0 |
| 10 | | | >300 | >300 | 168.0 | 170.0 |

[a]Platelets were incubated with test compound at 37° C. for 1 min, then thrombin (0.1 unit/mL), AA (100 μM), collagen (10 μg/mL) or PAF (2 ng/mL) was added to trigger the aggregation. Values are presented as the concentration (μM) by 50% inhibition of platelet aggregation ($IC_{50}$). Aspirin acts as a positive control. The accuracy of $IC_{50}$ values are within ± 10%.

In the present invention, we hoped to identify compounds with similar anti-platelet activity. Thus, the antiplatelet activities of all the synthesized compounds were determined and compared with the positive controls, YC-1 and 1-benzyl-3-(4-hydroxymethylphenyl)indazole (YD-1). In the following section, however, only the activity of a few representative compounds will be discussed. As indicated by the data in Table 1, the replacement of the indazole ring of YC-1 with indole yielded compound 7 with nearly no anti-platelet activity. Then, the substitution of the furan ring of compound 7 with thiophene ring (8) did not improve its activity either. Based on the above findings, it seems reasonable to assume that the $sp^2$-hybridized nitrogen of the indazole ring contributed significantly to the superior anti-platelet activity of the original YC-1.

Next, the replacement of the benzyl group of compound 7 with phenylsulfonyl group resulted in N-phenylsulfonyl derivatives (16) that, like YC-1, demonstrated significant inhibition against platelet aggregation induced by thrombin, AA, collagen and PAF.

Meanwhile, the replacement of the furan ring of compound 16 with thiophene ring (17) impaired its inhibitory activity toward thrombin-induced aggregation while maintained excellent inhibitory activity against AA-, collagen- and PAF-induced platelet aggregation.

In another approach, the substitution of the benzyl group of compound 7 with benzoyl group yielded compound 32 with activity profile slightly different from compound 16. Although compound 32 demonstrated excellent inhibitory activity toward AA- and collagen-induced platelet aggregation, it was inefficient as inhibitors for thrombin- and PAF-induced platelet aggregation. To the opposite, the introduction of an $OCH_3$ group, into the meta position of the benzoyl group of compound 32, afforded compound 33 with anti-platelet activity comparable with YC-1, and showed significant inhibition toward thrombin-, AA-, collagen- and PAF-induced platelet aggregation, Alternatively, if the $OCH_3$ group was displaced to the para position of the benzoyl group of compound 32 instead, the so formed compound 34 showed potent inhibition against AA- and collagen-induced platelet aggregation, but poor inhibition toward thrombin- and PAF-induced aggregation.

Finally, when compared the anti-platelet activity of the indole analogs of YD-1 (10) with its parent compound YD-1, it became clear that, unlike YD-1. Compound 10 only inhibited platelet aggregation triggered by collagen and PAF.

Although we have prepared few other compounds that also showed anti-platelet activity, their activity profile was determined to differ widely from that of YC-1. Hence the activity of these compounds was not included in Table 1, and will not be discussed here.

REFERENCES AND NOTES

1. Ko, F.-N.; Wu, C.-C.; Kuo, S.-C.; Lee, F.-Y; Teng, C.-M. *Blood*, 1994, 84, 4226.

2. Wu, C.-C.; Ko, F.-N.; Kuo, S.-C.; Lee, F.-Y.; Teng, C.-M. *Br. J. Pharmcol.* 1995, 116, 1973
3. Lee, F.-Y.; Lien, J. C.; Huang, T. M.; Tsai, S. C.; Teng, C.-M.; Wu, C.-C.; Cheng, F. C.; Kuo, S.-C. *J. Med. Chem.* 2001, 44, 3746.
4. Chun, Y S.; Yeo, E. J. *Park Cancer Lett.* 2004, 207, 1.
5. Brian, C.; Andrew, L.; Victor, S., *Org. Lett.,* 2002, 5, 815.

We claim:

1. A compound having the following formula (I):

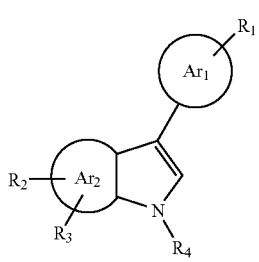

(I)

wherein $Ar_1$ is furyl, thiophene, or phenyl;
$Ar_2$ is benzene;
$R_1$ is hydroxyl C1–C6 alkyl,
$R_2$ and $R_3$ independently are H, Cl, F, Br, OH, or O—R;
$R_4$ is H, C1–C6 alkyl, or —Y—Ar, wherein Ar is C6–C14 aryl, Y is —$(CH_2)_n$—,

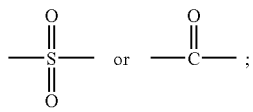

wherein R is C1–C6 alkyl, and n=1–6.

2. The compound as claimed in claim 1, wherein $Ar_1$ is furyl or thiophene.

3. The compound as claimed in claim 1, wherein $Ar_1$ is furyl.

4. The compound as claimed in claim 1, wherein $R_1$ is hydroxymethyl.

5. The compound as claimed in claim 1, wherein $R_2$ and $R_3$ are H.

6. The compound as claimed in claim 2, wherein $R_4$ is —Y—Ar.

7. The compound as claimed in claim 6, wherein $R_4$ is —Y-phenyl.

8. The compound as claimed in claim 7, wherein Y is

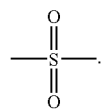

9. The compound as claimed in claim 7, wherein Y is

10. The compound as claimed in claim 1, wherein the compound (I) has the following structure:

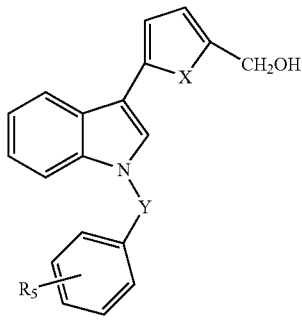

wherein X is O or S; Y and n are defined as in claim 1;
and $R_5$ is H, halogen, C1–C6 alkyl, or C1–C6 alkoxy.

11. The compound as claimed in claim 10, wherein X is O.

12. The compound as claimed in claim 11, wherein $R_5$ is H or C1–C6 alkoxy.

13. The compound as claimed in claim 12, wherein the C1–C6 alkoxy is methoxy.

14. The compound as claimed in claim 1, wherein the compound of formula (I) is N-benzenesulfonyl-3-(5'-hydroxymethyl-2'-furyl)indole (16), N-benzenesulfonyl-3-(5'-hydroxymethyl-2'-thienyl)indole (17),N-benzoyl-3-(5'-hydroxymethyl-2'-furyl)indole (32), N-(3'-methoxybenzoyl)-3-(5'-hydroxymethyl-2'-furyl)indole (33), or N-(4'-methoxybenzoyl)-3-(5'-hydroxymethyl-2'-furyl)indole (34).

* * * * *